United States Patent
Kurady et al.

(10) Patent No.: US 6,873,675 B2
(45) Date of Patent: Mar. 29, 2005

(54) MULTI-SECTOR BACK-OFF LOGIC ALGORITHM FOR OBTAINING OPTIMAL SLICE-SENSITIVE COMPUTED TOMOGRAPHY PROFILES

(75) Inventors: Rajendra Kurady, Waukesha, WI (US); Darin Okerlund, Muskego, WI (US); Mark Woodford, Waukesha, WI (US); Edward Henry Chao, Oconomowoc, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 275 days.

(21) Appl. No.: 10/323,256

(22) Filed: Dec. 18, 2002

(65) Prior Publication Data

US 2004/0120447 A1 Jun. 24, 2004

(51) Int. Cl.[7] .......................... G21K 1/12; G01N 23/00
(52) U.S. Cl. ......................................... 378/4; 378/901
(58) Field of Search ................................ 378/901, 4–20

(56) References Cited

U.S. PATENT DOCUMENTS

| | | | | |
|---|---|---|---|---|
| 6,587,539 B2 | * | 7/2003 | Oikawa ........................ | 378/19 |
| 6,665,370 B2 | * | 12/2003 | Bruder et al. ................. | 378/15 |
| 2002/0021785 A1 | * | 2/2002 | Toth et al. ................... | 378/147 |
| 2003/0185337 A1 | * | 10/2003 | Hsieh ........................... | 378/4 |

* cited by examiner

Primary Examiner—David V. Bruce
Assistant Examiner—Krystyna Suchecki
(74) Attorney, Agent, or Firm—Christopher L. Bernard, Esq.

(57) ABSTRACT

A multi-sector back-off logic algorithm for obtaining optimal slice-sensitive computed tomography ("CT") profiles. The systems and methods of the present invention improving the temporal resolution of a CT system by checking for Z location errors between sectors and automatically backing-off to an alternative multi-sector algorithm when necessary (i.e., selecting an optimized maximum number of sectors to reconstruct), providing less Z location error. Based upon this Z location error, the systems and methods of the present invention also calculating the maximum number of sectors that should be used for reconstruction "on-the-fly" (i.e., on a per image basis across an entire series of images). These systems and methods utilizing the Recommended Protocol for Cardiac Reconstruction Algorithms.

20 Claims, 4 Drawing Sheets

MULTI-SECTOR BACK-OFF LOGIC ALGORITHM FOR OBTAINING OPTIMAL SLICE-SENSITIVE COMPUTED TOMOGRAPHY PROFILES

FIELD OF THE INVENTION

The present invention relates generally to computed tomography ("CT") systems and methods. More specifically, the present invention relates to a multi-sector back-off logic algorithm for obtaining optimal slice-sensitive CT profiles, especially for cardiac applications.

BACKGROUND OF THE INVENTION

Computed tomography ("CT") systems are often used to image the heart and cardiovasculature. The data for a given image may be collected from multiple cardiac cycles using multiple sectors. This creates a number of challenges. In an ideal case, the multiple sectors used to reconstruct the heart and cardiovasculature overlap for a zero Z location error between sectors. This, however, is not always the case. For a relatively low heart rate and high pitch, for example, the sectors used to reconstruct the heart and cardiovasculature do not always overlap, resulting in a relatively large Z location error between sectors and relatively poor slice-sensitive profiles. Because of this, the data collected from multiple cardiac cycles may be too far apart, resulting in poor image quality.

Thus, what is needed are systems and methods that generate high temporal resolution images for cardiac CT applications while addressing the problem of bad images by checking for these Z location errors between sectors and automatically backing-off to an alternative multi-sector algorithm when necessary (i.e., selecting an optimized maximum number of sectors to reconstruct), providing less Z location error. What is also needed are systems and methods that, based upon this Z location error, calculate the maximum number of sectors that should be used for reconstruction "on-the-fly" (i.e., on a per image basis across an entire series of images). Preferably, these systems and methods utilize the Recommended Protocol for Cardiac Reconstruction Algorithms.

BRIEF SUMMARY OF THE INVENTION

Accordingly, the present invention provides a multi-sector back-off logic algorithm for obtaining optimal slice-sensitive computed tomography ("CT") profiles. The systems and methods of the present invention generate high temporal resolution images for cardiac CT applications and address the problem of bad images by checking for Z location errors between sectors and automatically backing-off to an alternative multi-sector algorithm when necessary (i.e., selecting an optimized maximum number of sectors to reconstruct), providing less Z location error. Based upon this Z location error, the systems and methods of the present invention also calculate the maximum number of sectors that should be used for reconstruction "on-the-fly" (i.e., on a per image basis across an entire series of images). These systems and methods utilize the Recommended Protocol for Cardiac Reconstruction Algorithms.

In one embodiment of the present invention, a computed tomography method includes determining a maximum Z location error and determining a weighted average Z location error. The computed tomography method also includes selecting a threshold value associated with the maximum Z location error and the weighted average Z location error. The computed tomography method further includes prescribing an N+1 sector reconstruction algorithm. If the maximum Z location error is less than or equal to the threshold value or the weighted average Z location error is less than or equal to the threshold value, the computed tomography method includes performing an N+1 sector reconstruction. If the maximum Z location error exceeds the threshold value or the weighted average Z location error exceeds the threshold value, the computed tomography method includes prescribing an N sector reconstruction.

In another embodiment of the present invention, a computed tomography method for obtaining optimal slice-sensitive profiles includes determining a maximum Z location error associated with a computed tomography system and determining a weighted average Z location error associated with the computed tomography system. The computed tomography method also includes selecting a threshold value associated with the maximum Z location error and the weighted average Z location error. The computed tomography method further includes prescribing an N+1 sector reconstruction algorithm. If the maximum Z location error is less than the threshold value or the weighted average Z location error is less than the threshold value, the computed tomography method includes performing an N+1 sector reconstruction. If the maximum Z location error exceeds the threshold value or the weighted average Z location error exceeds the threshold value, the computed tomography method includes prescribing an N sector reconstruction.

In an further embodiment of the present invention, an imaging method for obtaining optimal slice-sensitive profiles includes determining a maximum Z location error associated with an imaging system and determining a weighted average Z location error associated with the imaging system. The imaging method also includes selecting a threshold value associated with the maximum Z location error and the weighted average Z location error. The imaging method further includes prescribing an N+1 sector reconstruction algorithm. If the maximum Z location error is less than the threshold value or the weighted average Z location error is less than the threshold value, the imaging method includes performing an N+1 sector reconstruction. If the maximum Z location error exceeds the threshold value or the weighted average Z location error exceeds the threshold value, the imaging method includes prescribing an N sector reconstruction.

In a still further embodiment of the present invention, a computed tomography system includes a computed tomography scanner, a first algorithm operable for determining a maximum Z location error associated with the computed tomography system, and a second algorithm operable for determining a weighted average Z location error associated with the computed tomography system. The computed tomography system also includes a third algorithm operable for selecting a threshold value associated with the maximum Z location error and the weighted average Z location error. The computed tomography system further includes means for prescribing an N+1 sector reconstruction algorithm. The computed tomography system still further includes a fourth algorithm operable for, if the maximum Z location error is less than the threshold value or the weighted average Z location error is less than the threshold value, performing an N+1 sector reconstruction, and wherein the fourth algorithm is further operable for, if the maximum Z location error exceeds the threshold value or the weighted average Z location error exceeds the threshold value, prescribing an N sector reconstruction.

In a still further embodiment of the present invention, an imaging system includes an imaging scanner, a first algorithm operable for determining a maximum Z location error associated with the imaging system, and a second algorithm operable for determining a weighted average Z location error associated with the imaging system. The imaging system also includes a third algorithm operable for selecting a threshold value associated with the maximum Z location error and the weighted average Z location error. The imaging system further includes means for prescribing an N+1 sector reconstruction algorithm. The imaging system still further includes a fourth algorithm operable for, if the maximum Z location error is less than the threshold value or the weighted average Z location error is less than the threshold value, performing an N+1 sector reconstruction, and wherein the fourth algorithm is further operable for, if the maximum Z location error exceeds the threshold value or the weighted average Z location error exceeds the threshold value, prescribing an N sector reconstruction.

DETAILED DESCRIPTION OF THE INVENTION

Figure 1:
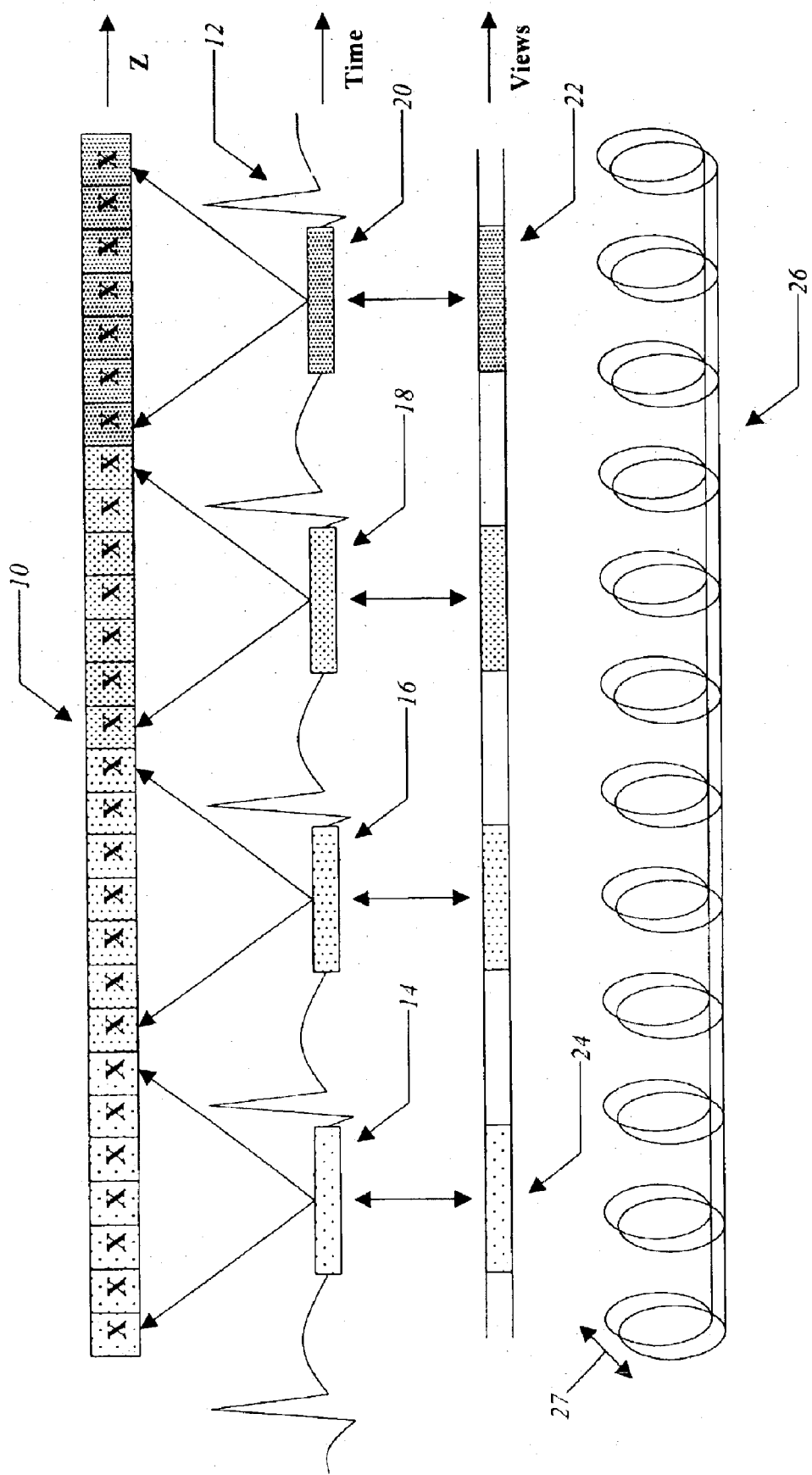
FIG. 1 is a schematic diagram illustrating a retrospectively EKG-gated reconstruction associated with the systems and methods of the present invention.

The systems and methods of the present invention allow for the creation of relatively high temporal resolution images for cardiac applications while addressing the problem of the generation of bad images due to relatively large Z location errors between sectors that are used for reconstruction. In general, the algorithm of the present invention is based upon the measurement of maximum Z location error ("ME") and weighted average Z location error ("WE") and determining how far these measurements are from predetermined limits.

The computation of the Z location error, ME, and WE includes a number of steps beginning with calculating half the detector coverage (i.e., the distance from the center of the detector to the center of the outer row). This is done using the following equation:

$$\text{half the detector coverage} = [(\text{num\_rows}/2) - 1] * \text{detector width.} \quad (1)$$

Next, the Z location error is computed for each sector. This is done by finding the Z location of the center view in the table space and calculating upper ("maximum") limit and the lower ("minimum") limit that the detector may cover at this particular Z location. The maximum limit and the minimum limit are given by:

$$\text{maximum limit} = \text{center } Z \text{ location} + \text{half the detector coverage,} \quad (2)$$

$$\text{minimum limit} = \text{center } Z \text{ location} - \text{half the detector coverage.} \quad (3)$$

The Z location error is computed for each sector using the following algorithm and is a signed value:

$$\text{if } Z \text{ location} < \text{lower limit, } Z \text{ location error} = \text{lower limit} - Z \text{ location;} \quad (4)$$

$$\text{if } Z \text{ location} > \text{upper limit, } Z \text{ location error} = \text{upper limit} - Z \text{ location;} \quad (5)$$

$$\text{if lower limit} < Z \text{ location} < \text{upper limit, } Z \text{ location error} = 0. \quad (6)$$

Next, the maximum error between the upper most and lower most error sectors is calculated. This also involves calculating the maximum and minimum errors within the set of sectors and the maximum error spread. The maximum error spread is given by:

$$\text{maximum error spread} = \text{maximum error} - \text{minimum error} = \max(Z_i - Z_{desired}) - \min(Z_i - Z_{desired}). \quad (7)$$

Next, WE is calculated using the average error weighted by the number of views in each sector:

$$WE = \text{total error over all sectors/total view over all sectors} = \text{sum}(0, \text{sector}-1)|Z_i - Z_{desired}| * Wi. \quad (8)$$

The percentage of image locations, or images, that fall into the gap is given by gap/(gap+overlap).

Referring to FIG. 1, in one embodiment of the present invention, a retrospectively EKG-gated reconstruction is illustrated. The retrospectively EKG-gated reconstruction provides a plurality of image locations 10 that vary as a function of Z location associated with predetermined points along an EKG cycle 12 that vary as a function of time. The predetermined points along the EKG cycle 12 include, for example, a first cycle 14, a second cycle 16, a third cycle 18, and a fourth cycle 20. The reconstruction algorithm of the present invention provides a continuous view stream 22 consisting of a plurality of view regions 24 utilized by the reconstruction algorithm. These view regions 24 correspond to the first cycle 14, the second cycle 16, the third cycle 18, and the fourth cycle 20. A plurality of detector rows 27 are used to obtain images as part of a low-pitch helical scan 26.

Figure 2:
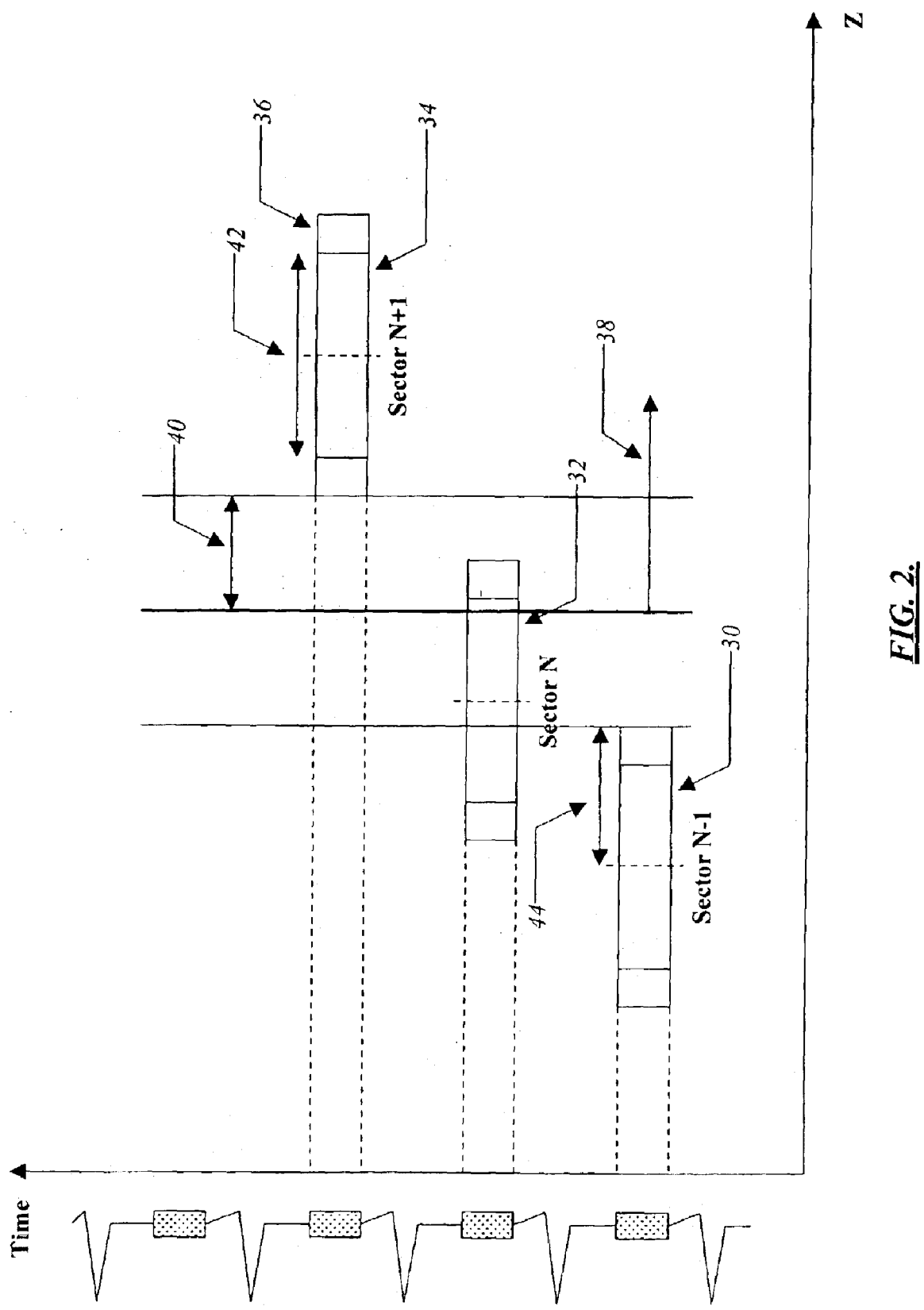
FIG. 2 is a graph illustrating the Z location error concepts associated with the systems and methods of the present invention.

In another embodiment of the present invention, the Z location error concepts described above are illustrated in FIG. 2. FIG. 2 shows a plurality of sectors, including a sector N−1 30, a sector N 32, and a sector N+1 34. Each sector includes a tolerance level 36. The Z location for a given image 38 and a Z location error >0 are also shown. Further, the half detector coverage 42 (i.e., 1.5 detector for a 4-row configuration, 3.5 detector for an 8-row configuration, 7.5 detector for a 16-row configuration) and the range 44 are also shown.

As described above, the multi-sector back-off logic algorithm for obtaining optimal slice-sensitive CT profiles of the present invention is based upon deciding the maximum number of sectors to reconstruct in a given situation. This determination is made based upon how far two given sectors are separated with respect to the Z location. The algorithm begins with a predetermined number of sectors and, based upon the maximum Z location error and the weighted average Z location error, backs off to a lesser number of sectors until images may be generated with minimum error. This algorithm is illustrated in FIG. 3.

Figure 3:
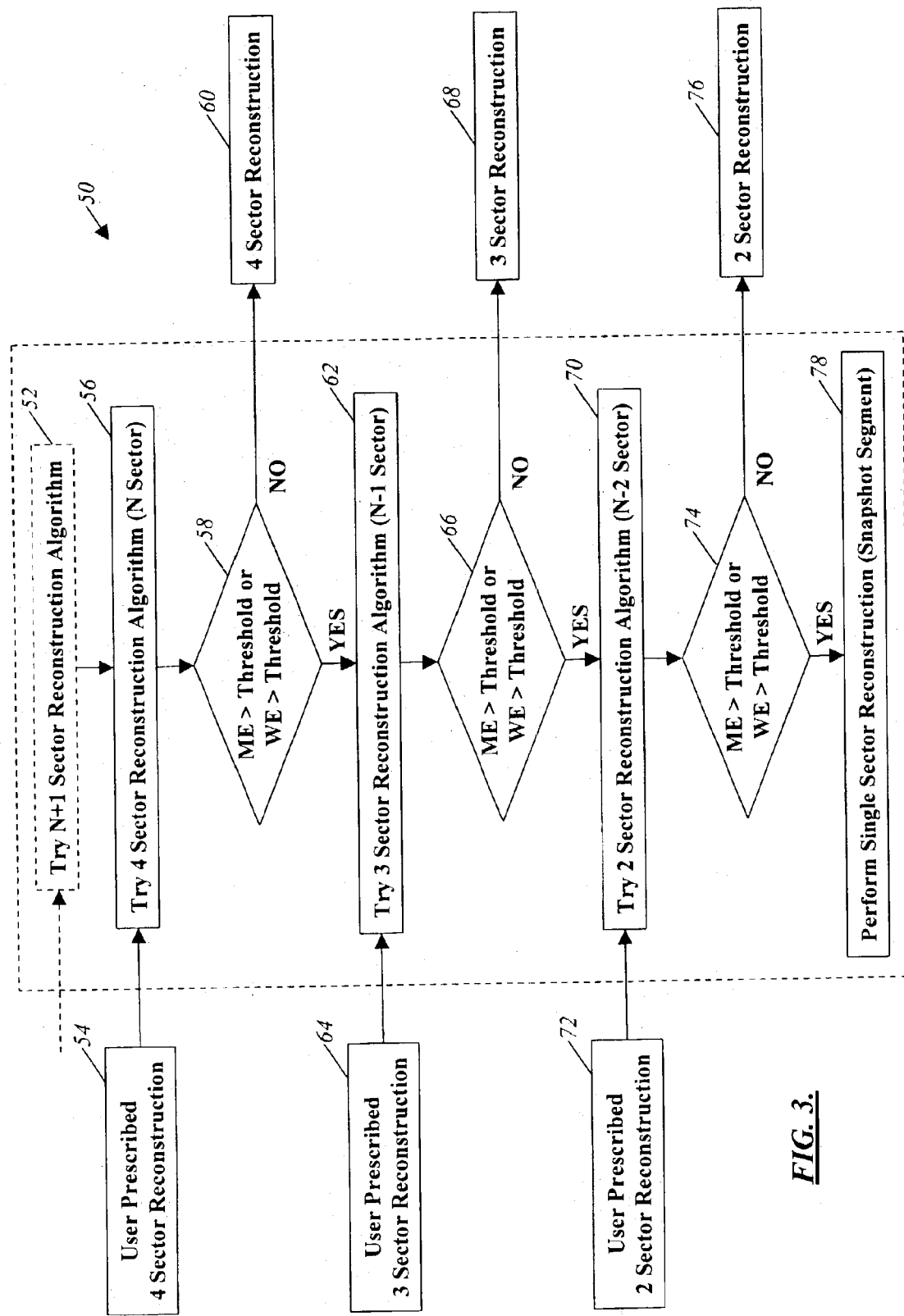
FIG. 3 is a flow chart illustrating one embodiment of the multi-sector back-off logic algorithm for obtaining optimal slice-sensitive CT profiles of the present invention.

Referring to FIG. 3, in a further embodiment of the present invention, the multi-sector back-off logic algorithm for obtaining optimal slice-sensitive CT profiles of the present invention 50 begins with the "auto burst" algorithm 50 trying an N+1 or N sector reconstruction algorithm 52,56. For example, a user may prescribe a four sector reconstruction 54 and the auto burst algorithm 50 may try a four sector (N sector) reconstruction algorithm 56. If ME is less than the threshold or WE is less than the threshold 58, then a four sector reconstruction is performed 60. If ME exceeds the threshold or WE exceeds the threshold 58, then the auto burst algorithm 50 tries a three sector (N−1 sector) reconstruction algorithm 62. This is also the starting point if the user prescribes a three sector reconstruction 64. If ME is less than the threshold or WE is less than the threshold 66, then a three sector reconstruction is performed 68. If ME exceeds the threshold or WE exceeds the threshold 66, then the auto burst algorithm 50 tries a two sector (N−2 sector) reconstruction algorithm 70. This is also the starting point if the user prescribes a two sector reconstruction 72. If ME is less than the threshold or WE is less than the threshold 74, then a two sector reconstruction is performed 76. If ME exceeds the threshold or WE exceeds the threshold 74, then the auto burst algorithm 50 performs a single sector reconstruction 78 (i.e., a snapshot segment).

Figure 4:
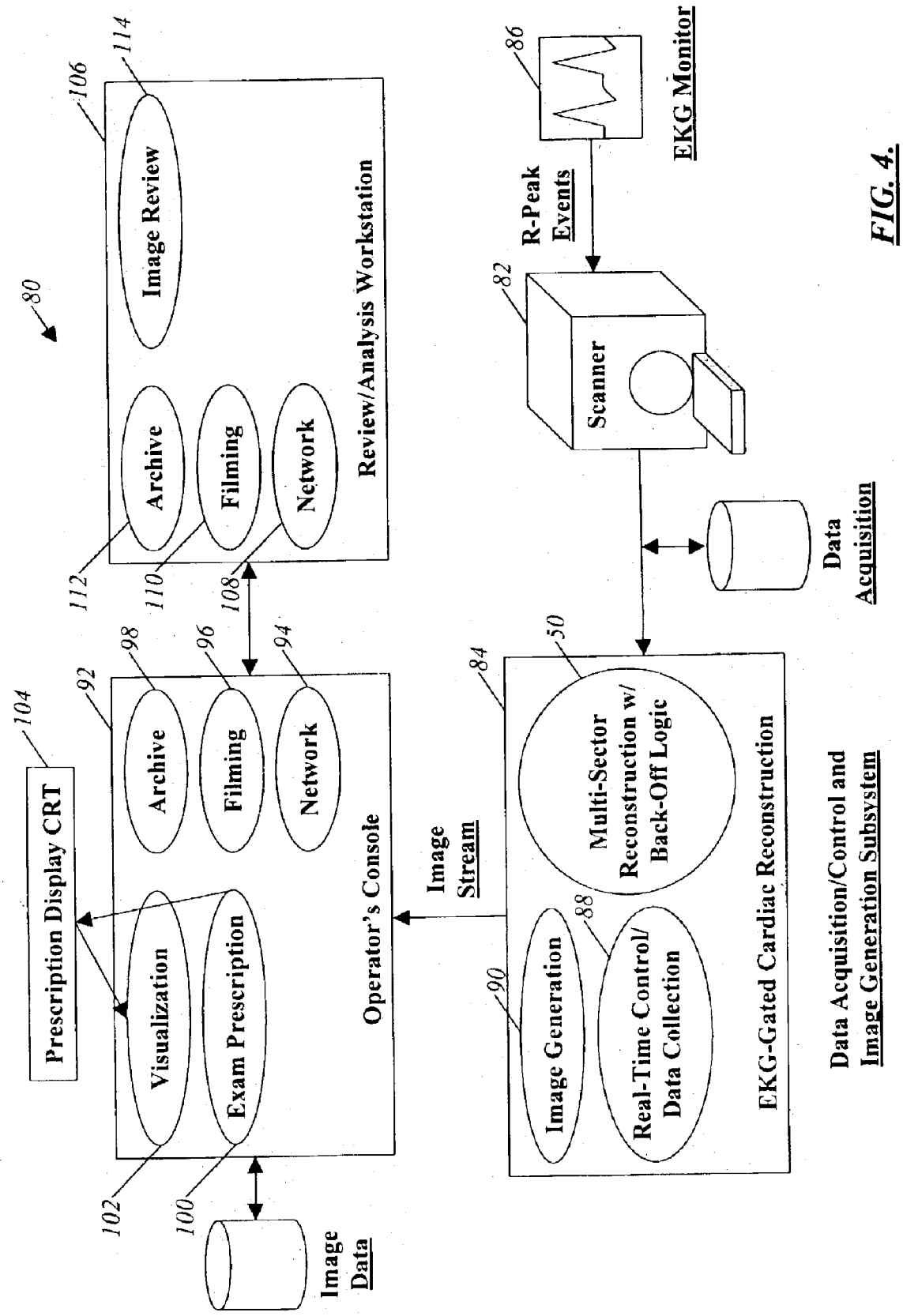
FIG. 4 is a schematic diagram illustrating one embodiment of a computed tomography ("CT") system incorporating the multi-sector back-off logic algorithm for obtaining optimal slice-sensitive CT profiles of the present invention.

Referring to FIG. 4, in a still further embodiment of the present invention, a CT system 80 incorporating the multi-sector back-off logic algorithm for obtaining optimal slice-sensitive CT profiles 50 includes a CT scanner 82 coupled to a data acquisition/control and image generation subsystem 84. Preferably, the CT scanner 82 is also coupled to an EKG monitor 86 or the like operable for measuring R-peak events or the like. The data acquisition/control and image generation subsystem 84 may be operable for performing, for example, an EKG-gated cardiac reconstruction. In order to do this, the data acquisition/control and image generation subsystem 84 includes a real-time control/data collection algorithm 88, the auto burst algorithm 50, and an image generation algorithm 90. The data acquisition/control and image generation subsystem 84 is operable for transmitting an image stream to an operator's console 92 or the like including a network component 94, a filming component 96, an archive component 98, an exam prescription component 100, and a visualization component 102. The exam prescription component 100 and the visualization component 102 may be associated with a prescription display CRT 104 or the like. The operator's console 92 is coupled to a review/analysis workstation 106 also including a network component 108, a filming component 110, and an archive component, as well as an image review component 114.

It is apparent that there has been provided, in accordance with the systems and methods of the present invention, a multi-sector back-off logic algorithm for obtaining optimal slice-sensitive CT profiles. Although the systems and methods of the present invention have been described with reference to preferred embodiments and examples thereof, other embodiments and examples may perform similar functions and/or achieve similar results. All such equivalent embodiments and examples are within the spirit and scope of the present invention and are intended to be covered by the following claims.

What is claimed is:

1. A computed tomography method, comprising:
   determining a maximum Z location error;
   determining a weighted average Z location error;
   selecting a threshold value associated with the maximum Z location error and the weighted average Z location error;
   prescribing an N+1 sector reconstruction algorithm;
   if the maximum Z location error is less than the threshold value or the weighted average Z location error is less than the threshold value, performing an N+1 sector reconstruction; and
   if the maximum Z location error exceeds the threshold value or the weighted average Z location error exceeds the threshold value, prescribing an N sector reconstruction.

2. The computed tomography method of claim 1, further comprising, if the maximum Z location error is less than the threshold value or the weighted average Z location error is less than the threshold value, performing an N sector reconstruction.

3. The computed tomography method of claim 2, further comprising, if the maximum Z location error exceeds the threshold value or the weighted average Z location error exceeds the threshold value, prescribing an N−1 sector reconstruction.

4. The computed tomography method of claim 1, wherein the computed tomography method is used to perform cardiac imaging.

5. A computed tomography method for obtaining optimal slice-sensitive profiles, comprising:
   determining a maximum Z location error associated with a computed tomography system;
   determining a weighted average Z location error associated with the computed tomography system;
   selecting a threshold value associated with the maximum Z location error and the weighted average Z location error;
   prescribing an N+1 sector reconstruction algorithm;
   if the maximum Z location error is less than the threshold value or the weighted average Z location error is less than the threshold value, performing an N+1 sector reconstruction; and
   if the maximum Z location error exceeds the threshold value or the weighted average Z location error exceeds the threshold value, prescribing an N sector reconstruction.

6. The computed tomography method of claim 5, further comprising, if the maximum Z location error is less than the threshold value or the weighted average Z location error is less than the threshold value, performing an N sector reconstruction.

7. The computed tomography method of claim 6, further comprising, if the maximum Z location error exceeds the threshold value or the weighted average Z location error exceeds the threshold value, prescribing an N−1 sector reconstruction.

8. The computed tomography method of claim 5, wherein the computed tomography method is used to perform cardiac imaging.

9. An imaging method for obtaining optimal slice-sensitive profiles, comprising:
   determining a maximum Z location error associated with an imaging system;
   determining a weighted average Z location error associated with the imaging system;
   selecting a threshold value associated with the maximum Z location error and the weighted average Z location error;
   prescribing an N+1 sector reconstruction algorithm;
   if the maximum Z location error is less than the threshold value or the weighted average Z location error is less than the threshold value, performing an N+1 sector reconstruction; and
   if the maximum Z location error exceeds the threshold value or the weighted average Z location error exceeds the threshold value, prescribing an N sector reconstruction.

10. The imaging method of claim 9, further comprising, if the maximum Z location error is less than the threshold value or the weighted average Z location error is less than the threshold value, performing an N sector reconstruction.

11. The imaging method of claim 10, further comprising, if the maximum Z location error exceeds the threshold value or the weighted average Z location error exceeds the threshold value, prescribing an N−1 sector reconstruction.

12. The imaging method of claim 9, wherein the computed tomography method is used to perform cardiac imaging.

13. A computed tomography system, comprising:

a computed tomography scanner;

a first algorithm operable for determining a maximum Z location error associated with the computed tomography system;

a second algorithm operable for determining a weighted average Z location error associated with the computed tomography system;

a third algorithm operable for selecting a threshold value associated with the maximum Z location error and the weighted average Z location error;

means for prescribing an N+1 sector reconstruction algorithm;

a fourth algorithm operable for, if the maximum Z location error is less than the threshold value or the weighted average Z location error is less than the threshold value, performing an N+1 sector reconstruction; and wherein the fourth algorithm is further operable for, if the maximum Z location error exceeds the threshold value or the weighted average Z location error exceeds the threshold value, prescribing an N sector reconstruction.

14. The computed tomography system of claim 13, wherein the fourth algorithm is further operable for, if the maximum Z location error is less than the threshold value or the weighted average Z location error is less than the threshold value, performing an N sector reconstruction.

15. The computed tomography system of claim 14, wherein the fourth algorithm is further operable for, if the maximum Z location error exceeds the threshold value or the weighted average Z location error exceeds the threshold value, prescribing an N−1 sector reconstruction.

16. The computed tomography system of claim 13, wherein the computed tomography system is used to perform cardiac imaging.

17. An imaging system, comprising:

an imaging scanner;

a first algorithm operable for determining a maximum Z location error associated with the imaging system;

a second algorithm operable for determining a weighted average Z location error associated with the imaging system;

a third algorithm operable for selecting a threshold value associated with the maximum Z location error and the weighted average Z location error;

means for prescribing an N+1 sector reconstruction algorithm;

a fourth algorithm operable for, if the maximum Z location error is less than the threshold value or the weighted average Z location error is less than the threshold value, performing an N+1 sector reconstruction; and wherein the fourth algorithm is further operable for, if the maximum Z location error exceeds the threshold value or the weighted average Z location error exceeds the threshold value, prescribing an N sector reconstruction.

18. The imaging system of claim 17, wherein the fourth algorithm is further operable for, if the maximum Z location error is less than the threshold value or the weighted average Z location error is less than the threshold value, performing an N sector reconstruction.

19. The imaging system of claim 18, wherein the fourth algorithm is further operable for, if the maximum Z location error exceeds the threshold value or the weighted average Z location error exceeds the threshold value, prescribing an N−1 sector reconstruction.

20. The imaging system of claim 17, wherein the imaging system is used to perform cardiac imaging.

\* \* \* \* \*